United States Patent
Lee et al.

(10) Patent No.: US 9,689,609 B2
(45) Date of Patent: Jun. 27, 2017

(54) PORTABLE BAG ASSEMBLY HAVING DRYING AND STERILIZATION FUNCTION

(71) Applicants: Sunjung Lee, Busan (KR); Seonhui Yoon, Busan (KR)

(72) Inventors: Sunjung Lee, Busan (KR); Seonhui Yoon, Busan (KR)

(73) Assignees: Sunjung Lee, Busan (KR); Hwa-Jung Lee, Busan (KR)

( * ) Notice: Subject to any disclaimer, the term of this patent is extended or adjusted under 35 U.S.C. 154(b) by 6 days.

(21) Appl. No.: 14/744,400

(22) Filed: Jun. 19, 2015

(65) Prior Publication Data

US 2016/0370112 A1 Dec. 22, 2016

(51) Int. Cl.
| | |
|---|---|
| *A61L 2/14* | (2006.01) |
| *F26B 9/00* | (2006.01) |
| *A61L 2/08* | (2006.01) |
| *A61L 2/24* | (2006.01) |

(52) U.S. Cl.
CPC .............. *F26B 9/003* (2013.01); *A61L 2/085* (2013.01); *A61L 2/14* (2013.01); *A61L 2/24* (2013.01)

(58) Field of Classification Search
USPC .................. 240/455.11; 250/455.11; 422/26
See application file for complete search history.

(56) References Cited

U.S. PATENT DOCUMENTS

| | | | | | |
|---|---|---|---|---|---|
| 4,906,103 | A * | 3/1990 | Kao | ...................... | A61J 1/2089 141/313 |
| 5,941,867 | A * | 8/1999 | Kao | ........................ | A61J 1/067 604/403 |
| 6,134,806 | A * | 10/2000 | Dhaemers | ............ | A43D 3/1491 34/202 |
| 6,422,061 | B1 * | 7/2002 | Sunshine | ............. | G01N 29/022 340/603 |
| 8,555,519 | B2 * | 10/2013 | McFarland | ............. | F26B 9/003 190/124 |

* cited by examiner

*Primary Examiner* — Phillip A Johnston
(74) *Attorney, Agent, or Firm* — Muncy, Geissler, Olds & Lowe, P.C.

(57) ABSTRACT

Disclosed herein is a portable bag assembly having a drying and sterilization function. The portable bag assembly includes a bag main body configured to form an inner space enabling an article to be received in and removed from the inner space, the partition unit having an openable surface so that access to the inner space is made; a partition unit contained in the bag main body to partition the inner space into multiple regions; a management unit provided in a portion of the bag main body to sterilize an article or to dry a wet article; a controller provided in a portion of the bag main body and electrically connected to the management unit, the controller controlling operation of the management unit; and a wireless communication module electrically connected to the controller to receive a control signal from a wireless terminal and transfer it to the controller.

6 Claims, 6 Drawing Sheets

| MANUFACTURING COMPANY | 2 | 4 | 7 | K | O | R | E | A | | |
|---|---|---|---|---|---|---|---|---|---|---|
| PRODUCT CODE | G | B | 1 | 0 | 0 | 4 | | | | |
| PRODUCTION YEAR | 2 | 0 | 1 | 5 | | | | | | |
| OPERATING TYPE | A | 1 | 1 | E | | | | | | |
| CONTROL SIGNAL INFORMATION | 2 | 7 | | | | | | | | |
| RESERVE | | | | | | | | | | |
| NUMBER OF BUTTONS | O | X | 0 | 8 | | | | | | |
| 1.BUTTON INFORMATION | 0 | 0 | 0 | 0 | 1 | 2 | : | 2 | 6 | : | 3 | 1 |
| 2.BUTTON INFORMATION | O | X | F | F | 3 | A | : | R | R | : | G | B |
| 3.BUTTON INFORMATION | O | 1 | O | N | | | : | F | A | : | 3 | 9 |
| ⋮ | | | | | | | | | | |

PORTABLE BAG ASSEMBLY HAVING DRYING AND STERILIZATION FUNCTION

BACKGROUND OF THE INVENTION

Field of the Invention

The present invention generally relates to a portable bag assembly having a drying and sterilization function and, more particularly, to a portable bag assembly having a drying and sterilization function, which is easy to carry and is configured to dry and sterilize articles put in the bag assembly in an inevitable situation in which the washing and drying of the articles are impossible, thus enabling the articles to be maintained in a sanitary state.

Description of Related Art

Recently, more and more people frequently visit facilities related to water, such as a swimming pool or spa, so as to enjoy recreational activities and conduct physical training.

In particular, upon using facilities such as a swimming pool or spa, most users generally move carrying wet articles, such as a wet swimming suit or underwear or various types of toiletries, in a portable bag or the like.

However, when wet articles are received in a sealed, dark, and compact space, such as the inside of a bag, water contained in the articles is combined with various types of harmful materials such as bacteria or mold, and then result in the growth of bacteria or the induction of odors.

From the standpoint of this disadvantage, there are conventional technologies.

However, those preceding technologies are configured to merely drain water contained in wet articles to the bottom of a bag, wherein the water is collected in a reservoir provided on the bottom surface of the bag and then drained. Accordingly, such conventional schemes have difficulty in sterilizing or drying wet articles due to the structural limitation thereof.

SUMMARY OF THE INVENTION

Accordingly, the present invention has been made keeping in mind the above problems occurring in the prior art, and an object of the present invention is to provide a portable bag assembly having a drying and sterilization function, which is easy to carry and is configured to dry and sterilize articles put in the bag assembly in an inevitable situation in which the washing and drying of the articles are impossible, thus enabling the articles to be maintained in a sanitary state.

In order to accomplish the above object, the present invention provides a portable bag assembly having a drying and sterilization function, including a bag main body configured to form an inner space enabling an article to be received in and removed from the inner space, the partition unit having an openable surface so that access to the inner space is made; a partition unit contained in the bag main body and configured to partition the inner space into multiple regions; a management unit provided in a portion of the bag main body and configured to sterilize an article received in the inner space or to dry a wet article by supplying cool air or warm air to the inner space; a controller provided in a portion of the bag main body and electrically connected to the management unit, the controller controlling operation of the management unit; and a wireless communication module electrically connected to the controller and configured to receive a control signal required for remote control of the management unit from a pre-designated wireless terminal and transfer the control signal to the controller.

The portable bag assembly may further include a two-dimensional (2D) barcode printed on a side surface of the bag main body and configured to record predetermined identification code in the 2D barcode, wherein the 2D barcode is scanned via a camera of the wireless terminal and configured to provide a remote control interface for generating the control signal to the wireless terminal.

The identification code recorded in the 2D barcode may be an address of a website composed of characters, and the remote control interface may be a mobile application downloaded from the website.

The identification code recorded in the 2D barcode may be a remote control information format functionally corresponding to an input button of the controller, and the remote control information format may be extended and registered in a remote control program previously installed in the wireless terminal and configured to provide the remote control interface.

The portable bag assembly may further include a humidity sensor provided in a portion of the bag main body and configured to measure humidity of the inner space. Here, the controller may determine whether the article received in the inner space has been dried by comparing humidity data measured by the humidity sensor with a preset reference value, and if it is determined that drying of the article has been completed, transmit a drying completion signal to the wireless terminal.

With these and other objects, advantages, and features of the invention that may become hereinafter apparent, the nature of the invention may be more clearly understood by reference to the detailed description of the invention, the embodiments and to the several drawings herein.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PREFERRED EMBODIMENTS

The advantages and features of the present invention and a method of achieving them will be more clearly understood from the detailed description of the following embodiments taken in conjunction with the accompanying drawings.

However, the present invention may be implemented in various forms without being limited by the following embodiments.

The present embodiments are intended to make the disclosure of the present invention complete and to completely notify those skilled in the art of the scope of the invention.

Further, the present invention is merely defined by the scope of the accompanying claims.

Therefore, in some exemplary embodiments, detailed descriptions of well-known components, operations, and technologies are omitted in order to avoid being construed as vague.

In the following description of the present invention, the same reference numerals are used to designate the same or similar elements, and the terms used (stated) in the present specification are merely used to describe specific embodiments and are not intended to limit the present invention.

In the present specification, a singular expression includes a plural expression unless a description to the contrary is specifically pointed out in context, and components and operations defined by the terms such as "include" (or "have") are not intended to exclude a possibility that one or more other components and operations will be present or added.

Unless differently defined, all terms used in the present specification (including technical and scientific terms) have the same meanings as the terms generally understood by those skilled in the art to which the present invention pertains.

The terms defined in generally used dictionaries are not interpreted as being ideal or excessively formal meanings unless they are definitely defined in the present specification.

Hereinafter, embodiments of the present invention will be described in detail with reference to the attached drawings.

Figure 1:
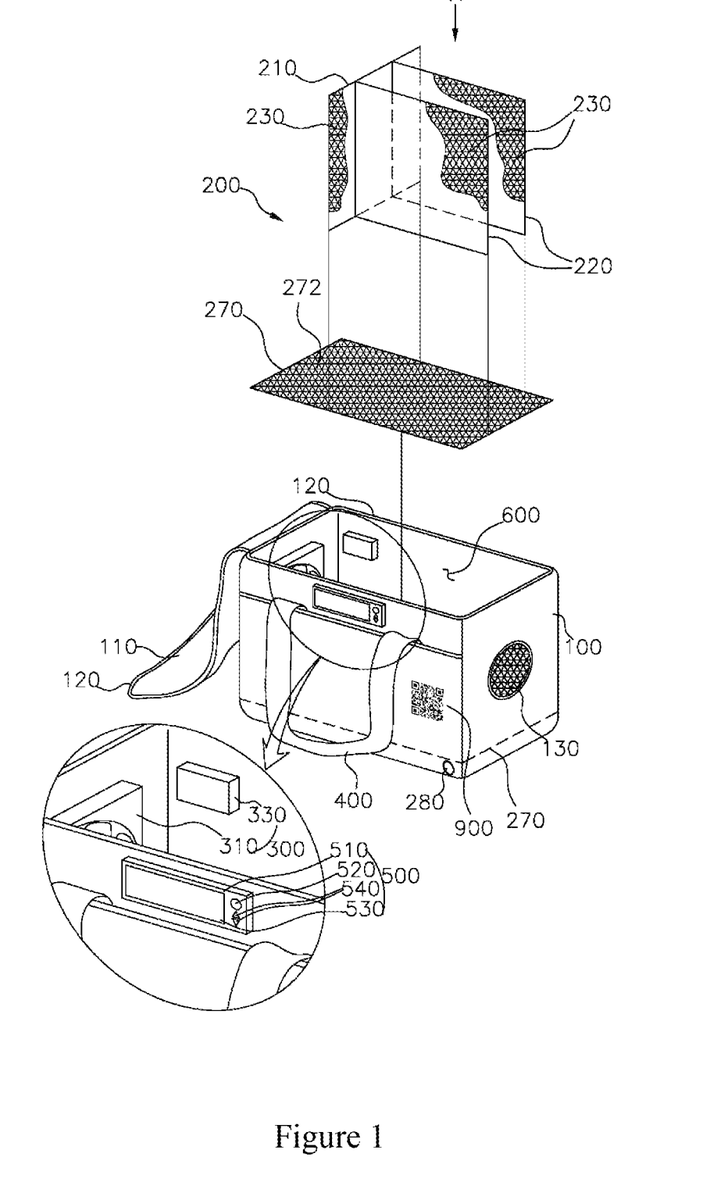
FIG. 1 is an exploded perspective view showing the overall structure of a portable bag assembly having a drying and sterilization function according to an embodiment of the present invention.

FIG. 1 is an exploded perspective view showing the overall structure of a portable bag assembly having a drying and sterilization function according to an embodiment of the present invention.

For reference, reference numeral 400 denotes a handle.

As shown in the drawing, it may be understood that the present invention has a configuration in which a partition unit 200 is contained in a bag main body 100 and in which a management unit 300 operated by a controller 500 and a wireless communication module 700 (see FIG. 5) for remotely receiving a control signal are provided in the bag main body 100.

In the bag main body 100, an inner space 600 enabling articles to be received in and removed from the inner space is formed, and the bag main body 100 has an openable surface to enable access to the inner space 600.

The partition unit 200 is contained in the bag main body 100, and is configured to partition the inner space 600 into multiple regions. Such a partition unit 200 enables various types of articles, for example, a towel, toiletries or a swimming suit, before or after being used, to be separately received in the individual regions of the partitioned inner space 600.

The management unit 300 is provided in a portion of the bag main body 100 to function to sterilize articles received in the inner space 600 or dry wet articles by supplying cool air or warm air to the inner space 600.

The controller 500 is provided in a portion of the bag main body 100, is electrically connected to the management unit 300, and is configured to control the operation of the management unit 300.

The wireless communication module 700 is electrically connected to the controller and is configured to receive a control signal required for remote control of the management unit from a pre-designated wireless terminal and to transfer the control signal to the controller.

Therefore, the portable bag assembly of the present invention is easy to carry in such a way that a user carries the portable bag assembly while holding the handle 400. Further, the portable bag assembly functions to provide assistance so that a sanitary state may be maintained by temporarily drying and sterilizing wet articles, such as underwear or a swimming suit, received in the bag in an inevitable situation in which it is impossible to wash and dry such wet articles. In addition, a drying or sterilization operation may be remotely controlled by connecting the wireless communication module 700 to a wireless terminal 800, thus providing user convenience.

The above embodiment may be applied to the present invention, and the following various embodiments may also be applied to the present invention.

First, in the present invention, a cover 110, which is extended from one edge of an open top surface of the bag main body 100 and is used to open and close the top surface, is provided so that accessibility to the inner space 600, that is, convenience allowing the user to easily insert and remove various articles into and from the inner space 600, may be provided.

Here, a zipper 120 for connecting the edges of the cover 110 to the edges of the open top surface is provided on the bag main body 100, and a slider (not shown) for opening/closing the top surface while reciprocating along a direction in which the zipper 120 is formed may be provided on the zipper 120.

In this case, in the side surface of the bag main body 100, an exhaust port 130 is preferably formed to discharge air circulated by the fan 310 of the management unit 300, which will be described later, to the outside of the bag main body.

Meanwhile, although not shown in the drawing, a pillar dry bar formed lengthwise in one direction may be disposed in the bag main body 100. A drying target, for example, a wet swimming suit or a damp pet item, is hung on the dry bar. Silver nanoparticles may be applied on the surface of the dry bar and sterilization effect for the drying target may be expected owing to the silver nanoparticles.

Further, the bag main body 100 is made of a fabric material. In particular, in the present embodiment, at least a partial region of the bag main body 100 may be made of fabric dyed by a heat-sensitive paint. The heat-sensitive paint is a dye, the color of which changes according to the temperature or humidity. Therefore, the user may predict the internal temperature or humidity of the bag main body 100 using the color of the heat-sensitive paint, thus predicting the dried state of articles received in the bag main body 100. For example, when the color of the heat-sensitive fabric is a color corresponding to high temperature, it may be determined that the articles are being dried, whereas when the color of the heat-sensitive fabric is a color corresponding to low temperature, it may be determined that the drying of the articles has been completed.

Figure 2:
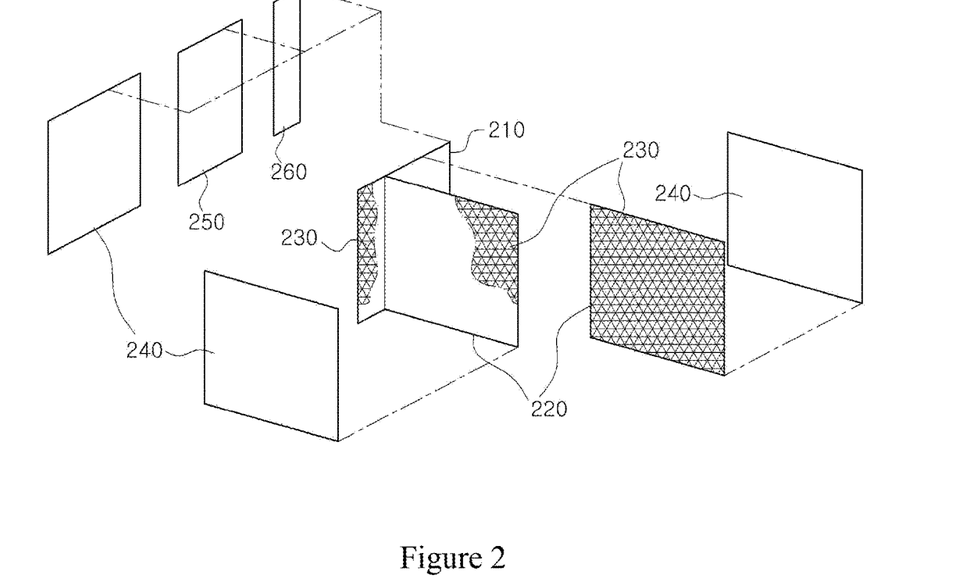
FIG. 2 is an exploded perspective view showing the coupling of a partition unit that is a principal part of the portable bag assembly having a drying and sterilization function according to an embodiment of the present invention.
Figure 3:
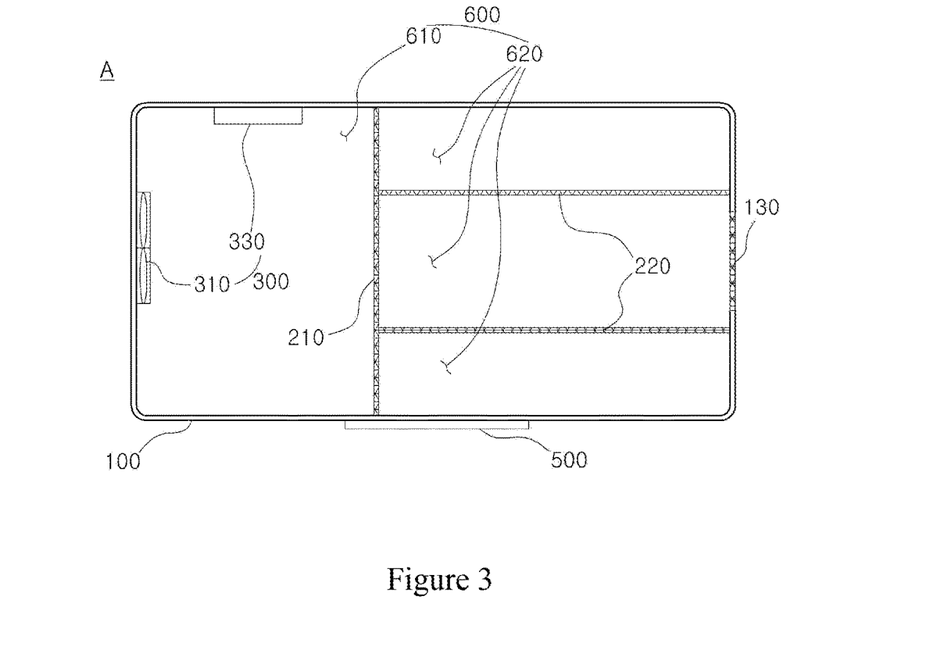
FIG. 3 is a planar conceptual view illustrating the internal structure of the portable bag assembly viewed from viewpoint A of FIG. 1.

Next, the partition unit 200 is configured to partition the inner space 600 into multiple regions, as shown in FIGS. 1 to 3, and to cause various articles to be obviously received in the respective regions. It may be considered that the partition unit 200 has a structure chiefly including a main frame 210 and sub-frames 220.

The main frame 210 is contained in the bag main body 100, and is used to partition the inner space 600 into a first space 610 and a second space 620.

As the sub-frames 220, one or more sub-frames 220 are contained in the first space 610 or the second space 620, are arranged to be orthogonal to the main frame 210, and are used to partition the first space 610 or the second space 620 into two or more regions.

Therefore, the main frame 210 and the sub-frames 220 allow the passage of cool air or warm air supplied from the management unit 300 to be selectively permitted.

For example, in the first space 610 partitioned and defined by the main frame 210, toiletries such as a toothbrush, a tube of toothpaste, or a bottle of shampoo, or swimming-related articles such as a swimming cap or swimming goggles, may be received and then be sterilized by the management unit 300. In the second space 620 partitioned by the sub-frames 220, articles such as a towel or a swimming suit may be received.

Here, the partition unit 200 may further include net-sheets 230 which are mounted on the main frame 210 and the sub-frames 220 and in which a mesh allowing the flow of air is entirely formed, in order to permit the passage of cool air or warm air.

When there is a need to block the passage of cool air or warm air, that is, when air containing moisture is transferred together and articles have already been dried during a drying procedure, or in order to prevent water from moving to articles before use, the partition unit 200 may further include a planar blocking plate 240 detachably coupled to the main frame 210 and the sub-frames 220 to be selectively replaceable and configured to block the flow of air.

That is, as shown in FIG. 2, the blocking plate 240 may selectively block the entirety or part of the area of the main frame 210 and the sub-frames 220, thus enabling the inflow and flow of cool air or warm air to be selectively permitted or blocked, as described above.

More specifically, in the partition unit 200, any of a large-scale blocking plate 240 for blocking the entire area of the main frame 210 or the sub-frames 220, a medium-scale blocking plate 250 for blocking most part of the area of the main frame 210 or the sub-frames 220, and a small-scale blocking plate 260 for blocking a part of the area of the main frame 210 or the sub-frames 220 may be selected and mounted, and then be used.

Here, detachable coupling between the main frame 210 and the sub-frames 220 may be implemented using various structures. It is apparent that applications and modification designs are possible in such a way that respective edges of the main frame 210 and the sub-frames 220 are slidably coupled to a rail (not shown) that crosses the edges or any locations of the main frame 210 and the sub-frames 220.

In this regard, as the blocking plate 240, the medium-scale blocking plate 250, and the small-scale blocking plate 260, any type of structures may be adopted and used as long as the structures enable each blocking plate to be slidably coupled to a rail, or to be detachably coupled using a permanent magnet, a hook button, Velcro, or the like.

Meanwhile, the fact that the above-described partition unit 200 is contained in the bag main body 100 means that the partition unit 200 may be detachably configured. Here, part of the partition unit 200 may be separated and attached/detached or, alternatively, the entirety thereof may be integrated and attached/detached. That is, at least a part of the partition unit 200 is attached or detached, so that customized drying suitable for the volume of dry targets is possible.

Preferably, the portable bag assembly of the present invention may further include a bottom frame 270 so that water from wet articles may be easily drained to the bottom surface of the bag main body 100, wherein the bottom frame 270 is arranged to be spaced apart from the bottom surface of the bag main body 100 by a predetermined distance, and is configured such that the main frame 210 and the sub-frames 220 are seated on the top surface of the bottom frame 270, and such that a mesh 272 for draining water to the bottom surface of the bag main body 100 is entirely formed.

Together with the bottom frame 270, the present invention may preferably further include a cover part (not shown) formed to be openable while penetrating through the side surface of the bag main body 100 near the bottom surface of the bag main body 100; and a drain hole 280 (see FIG. 1) configured to drain moisture drained through the bottom frame 270 to the outside of the bag main body 100.

Next, as described above, it can be seen that the management unit 300 performs sterilization and drying, and chiefly includes a fan 310, an electric heater 320 (see FIG. 4), and a sterilizer 330.

Figure 4:
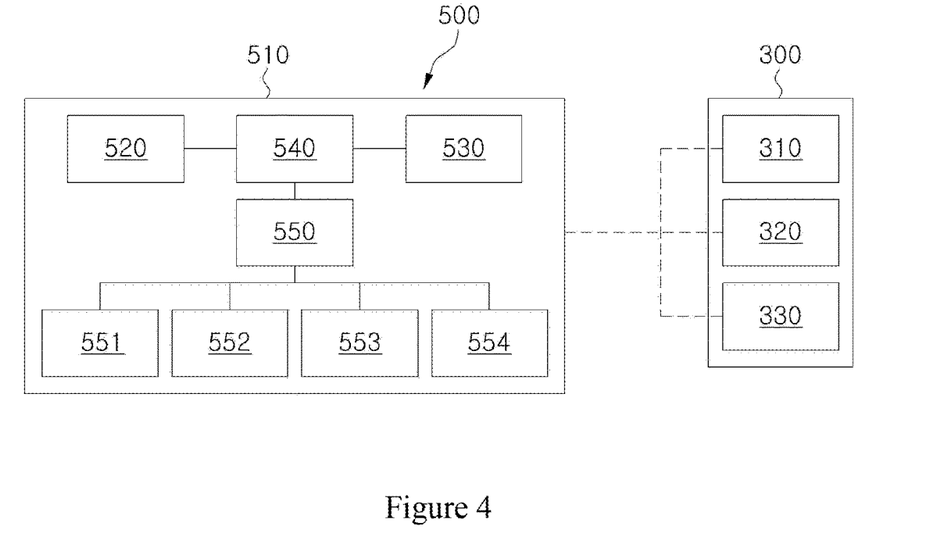
FIG. 4 is a block diagram showing an electrical connection between a management unit and a controller that are principal parts of the portable bag assembly having a drying and sterilization function according to an embodiment of the present invention.

The fan 310 is mounted in a portion of the bag main body 100 to circulate air through the inner space 600, and is configured to induce forced convection of air within the inner space 600.

The electric heater 320, which is mounted in the inner space 600 to heat or cool air in the inner space 600, employs a Peltier device (not shown) using a Peltier effect.

Therefore, the electric heater 320 may enable selective operation such that the heating part of the Peltier device is connected to the fan 310 and causes warm air to be discharged via the fan 310, or such that the cooling part of the Peltier device is connected to the fan 310 and causes cool air to be discharged via the fan 310.

In this case, the electric heater 320 is not limited by a specific structure and shape. It is apparent that the electric heater 320 may be operated using the Peltier device, and applications and modifications are also possible in such a way as to cause cool air to be discharged by adjusting the number of rotations of the fan 310 or to generate warm air by arranging a heat wire (not shown) in the inner space 600 of the bag main body 100 and compulsorily convecting heated air via the fan 310.

The sterilizer 330 is mounted in the inner space 600 and configured to radiate light having an infrared wavelength or emit negative ions to articles received in the inner space 600. For this structure, the employment of a Light Emitting Diode (LED) for radiating light having an infrared wavelength or emitting negative ions while reducing power consumption may be taken into consideration.

Therefore, the fan 310, the electric heater 320, and the sterilizer 330 may be electrically connected to the controller 500 and may then be operated either simultaneously or individually.

Next, the controller 500 is configured to control the operation of the management unit 300 including the fan 310, the electric heater 320, and the sterilizer 330, as described above. First, referring to a magnified portion of FIG. 1, it can be seen that the controller has a structure including a main body 510, an ON/OFF switch 520, a display panel 530, and a manipulation switch 540.

The main body 510, which is mounted in a portion of the bag main body 100 and is electrically connected to the management unit 300, provides a space and an area in which the individual components of the controller 500, which will be described later, are to be mounted.

The main body 510 is arranged at the location that can be easily and visually perceived and conveniently manipulated by the user.

The ON/OFF switch 520 is provided in the main body 510 to supply power to the management unit 300. It is apparent that the supply of power may be implemented using Universal Serial Bus (USB) power, commercial power, or power obtained from a rechargeable battery or the like.

The display panel 530 is configured in the main body 510 to display the operating status of the management unit 300.

The manipulation switch 540 is provided on the main body 510 to select the type-based operation of the management unit 300 or control airflow and the temperature and operating time of the inner space 600.

Below, the controller 500 will be described in detail with reference to FIG. 4. Preferably, the controller 500 may further include a mode selection unit 500 that is capable of supplying power to the fan 310, the electric heater 320, and the sterilizer 330, selecting the individual operations thereof, and adjusting drying, sterilization, and operation times.

It can be seen that such a mode selection unit 550 is contained in the main body 510 and includes a power supply controller 551, a cool/warm dry mode controller 552, a sterilization mode controller 553, and a timer 554.

The power supply controller 551 is electrically connected to the fan 310, the electric heater 320, and the sterilizer 330 to control a series of operations for supplying power to the entire management unit 300.

The cool/warm dry mode controller 552 is electrically connected to the fan 310 and the electric heater 320 to control a series of operations for controlling the operation of the fan 310 and the electric heater 320 so that cool air or warm air is selectively supplied to the inner space 600.

The sterilization mode controller 553 is electrically connected to the sterilizer 330 to control a series of operations for controlling the operation of the sterilizer 330 so that infrared wavelength light is radiated or negative ions are emitted to the inner space 600.

The timer 554 is electrically connected to the fan 310, the electric heater 320, and the sterilizer 330 to control a series of operations for setting the operating times of the fan 310, the electric heater 320, and the sterilizer 330.

Next, as described above, the wireless communication module 700 is configured to receive a control signal for remote control of the management unit from a pre-designated wireless terminal 800. It can be seen from FIG. 5 that the wireless communication module 700 receives a control signal from the wireless terminal 800 and transfers it to the controller 500.

Figure 5:
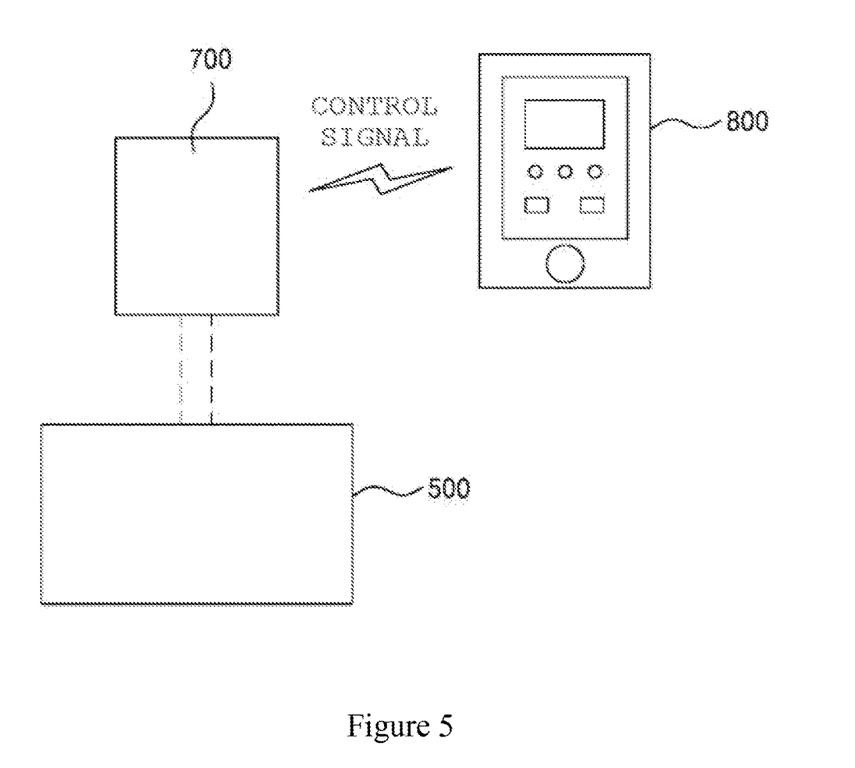
FIG. 5 is a block diagram showing an electrical connection between the controller and a wireless communication module that are principal parts of the portable bag assembly having a drying and sterilization function according to an embodiment of the present invention.

The wireless communication module 700 may be basically mounted in an initial production stage, or may be detachably coupled to the controller 500 in an external type and electrically connected to the controller 500.

Here, the wireless communication module 700 may be a component supporting both short-range communication and long-range communication. For short-range communication, a Bluetooth or Near-Field Communication (NFC) module may be installed in the portable bag assembly and may be connected to the wireless terminal 800 within a predetermined range and then transmit and receive data to and from the wireless terminal 800. For long-range communication, a mobile communication network module may be used and may then be connected to the wireless terminal 800 and transmit and receive data to and from the wireless terminal 800 without restrictions of distance and place.

Meanwhile, the portable bag assembly may further include a two-dimensional (2D) barcode 900 (see FIG. 1) which is printed on one surface of the bag main body 100 and in which predetermined identification code is recorded. Here, the 2D barcode 900 may be scanned via the camera of the wireless terminal 800 to provide a remote control interface for generating the control signal to the wireless terminal.

Such a 2D barcode 900 represents information in a rectangle using braille code or mosaic code, and the types of 2D barcodes include a Quick Response (QR) code, a data matrix, a Portable Data File (PDF) 417, and MaxiCode. In the present embodiment, it is preferable to use QR code and a data matrix so that an operation is facilitated in the camera recognition environment of the wireless terminal 800. Further, the 2D barcode is maintained in a state permanently printed on one surface of the bag main body 100, thus allowing the user to easily check the 2D barcode anytime. Further, it is apparent that the 2D barcode is implemented to be printed on a separate sticker or card, thus allowing the user to personally determine the location at which the sticker or card is to be attached, or carry the sticker or card.

Figure 6:
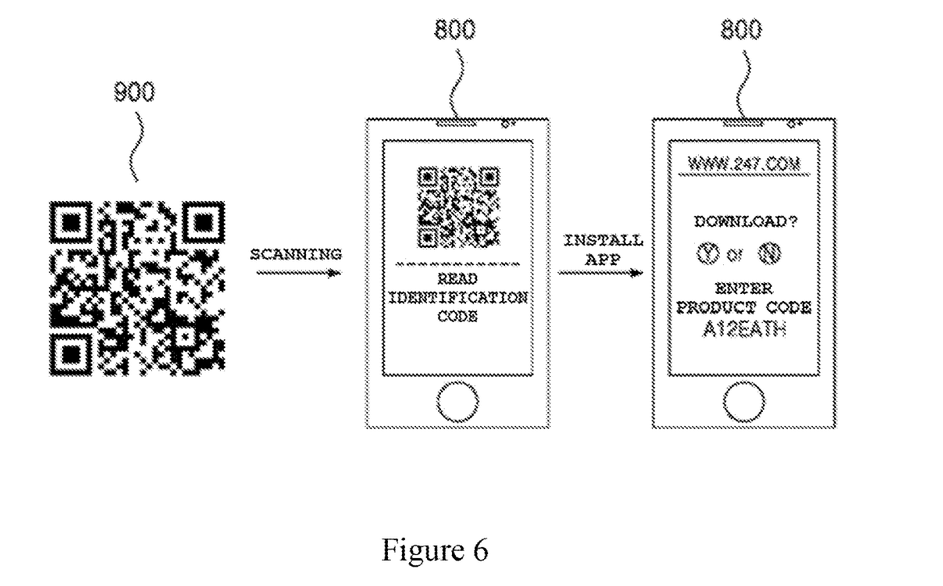
FIG. 6 is a conceptual view showing the principle of application of a 2D barcode according to an embodiment of the present invention.

Here, the identification code recorded on the 2D barcode 900 may be the address of a website composed of characters. Referring to FIG. 6, when the identification code of the 2D barcode 900 is recognized via scanning, a web browser installed in the wireless terminal 800 is executed to access the corresponding website, and an application registered on the website may be downloaded and installed according to the selection by the user. That is, the remote control interface may be a mobile application downloaded from the website, and may generate a control signal via the application to enable remote control to be performed.

Meanwhile, the ID code recorded on the 2D barcode 900 may be a remote control information format (see FIG. 7) functionally corresponding to the input button of the controller 500. At this time, the remote control information format may be extended and registered in a remote control program previously installed on the wireless terminal 800 to provide the remote control interface. Here, information about the arrangement and functions of input buttons is generated via the remote control information format illustrated in FIG. 7 using a remote control program previously installed in the wireless terminal 800, without accessing a website and downloading an application as in the case of the above example.

Figure 7:
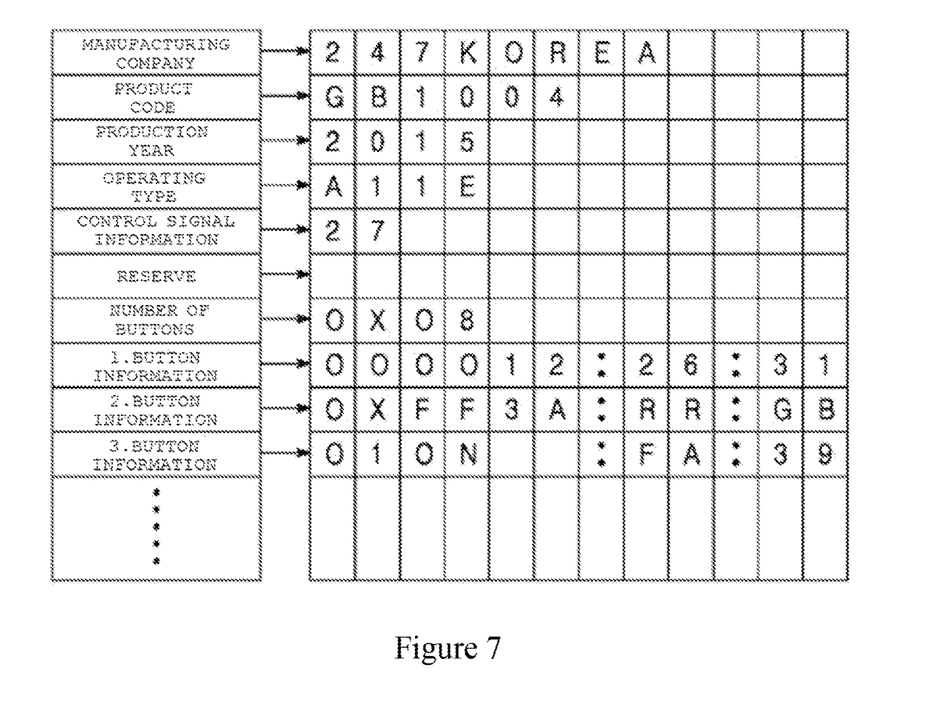
FIG. 7 is a conceptual view showing the principle of application of a 2D barcode according to another embodiment of the present invention.

That is, since the entire information required to generate the remote control interface may be recorded in the 2D barcode 900, the remote control information format may be extended and registered in the wireless terminal 800 without accessing the Internet. Therefore, since there is no burden on data use fees unintended by the user, and an Internet access procedure and a download procedure may be omitted, processing speed required to generate a remote control interface may be improved.

Although not shown in the drawing, the portable bag assembly may further include a humidity sensor provided in a portion of the bag main body 100 and configured to measure the humidity of the inner space. Here, the controller 500 determines whether articles received in the inner space have been dried by comparing humidity data measured by the humidity sensor with a preset reference value, and then transmits a drying completion signal to the wireless terminal 800 if it is determined that the drying of the articles has been completed. Therefore, the user may easily determine at any time or any place whether the drying of articles has been completed without continuously checking the state of the articles.

Hereinafter, examples of the actual operation of the portable bag assembly having a drying and sterilization function according to various embodiments of the present invention will be described in brief with reference to FIGS. 8 to 10.

Figure 8:
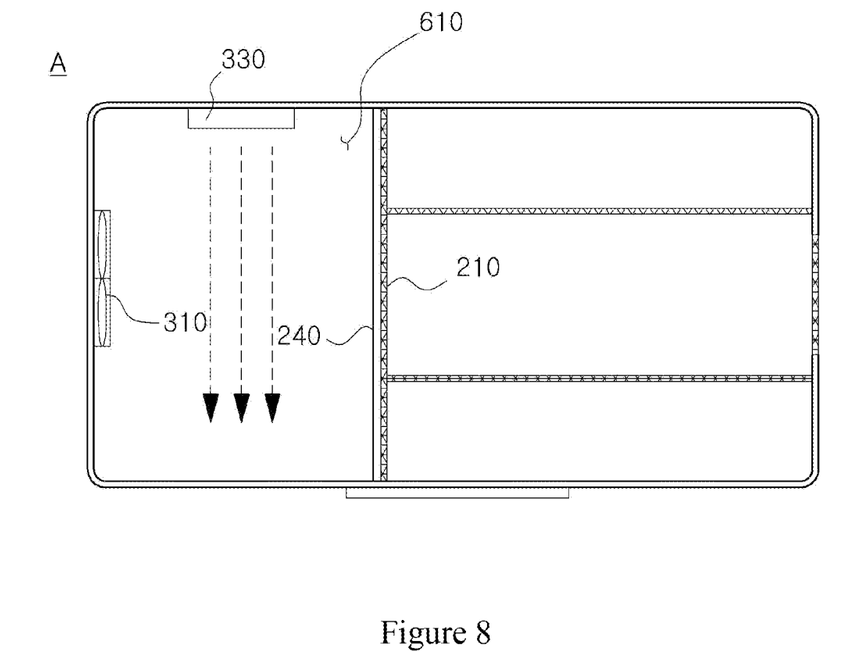
FIG. 8 to 10 are planar conceptual views illustrating the operating status of the portable bag assembly having a drying and sterilization function according to various embodiments of the present invention.
Figure 9:
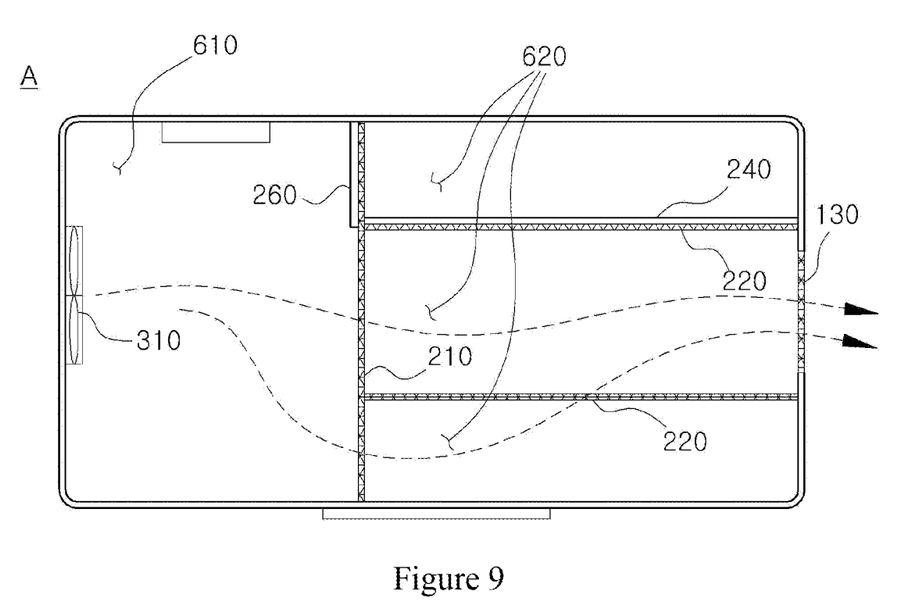
Figure 10:
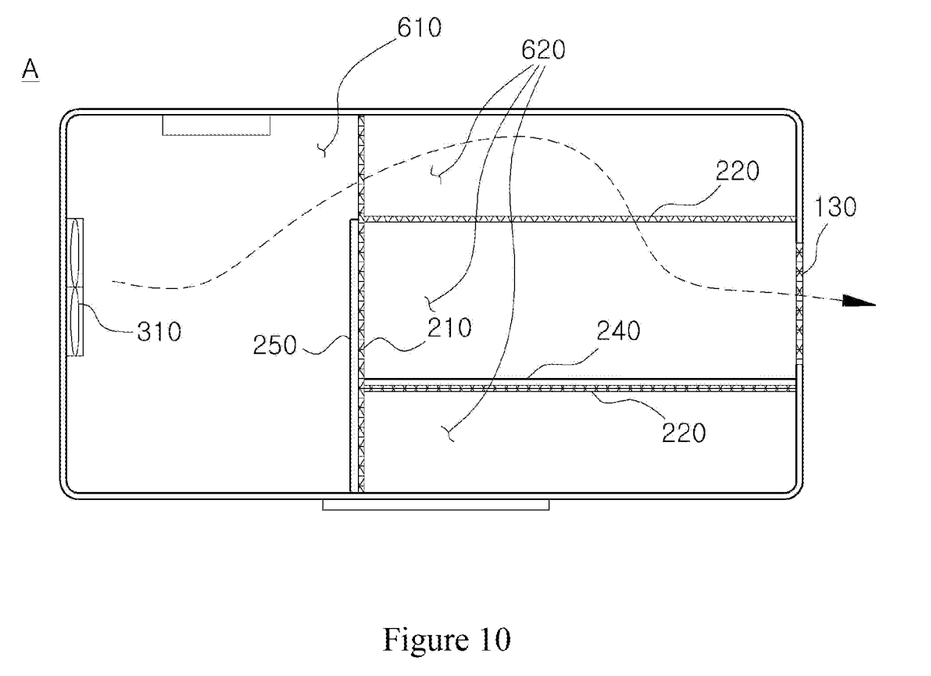

For reference, as reference numerals, not described in FIGS. 8 to 10, reference numerals shown in FIGS. 1 to 6 may be referred to.

First, prior to manipulating the controller 500, the user intends to sterilize articles such as a toothbrush, a tube of toothpaste, a bottle of shampoo, a swimming cap, or swimming goggles received in the first space 610 of the inner space 600 partitioned by the main frame 210.

However, when no articles are received in the second space 620 or when the received articles have already been dried, the user may install the blocking plate 240 for blocking the entire surface of the main frame 210 in the second space 620, manipulate the manipulation switch 540 of the controller 500, select the sterilization mode controller 553 from the mode selection unit 550, and then operate the sterilizer 330.

Meanwhile, when previously dried articles such as a towel or underwear that that has not yet been worn, are received in any one region of the second space 620 partitioned into multiple regions, the user couples the small-scale blocking plate 260 to the main frame 210, as shown in FIG. 2, so as to block the corresponding region, and couples the blocking plate 240 to the sub-frames 220, thus causing the corresponding region to be sealed.

Then, the user selects the cool/warm dry mode controller 552 from the mode selection unit 550 by manipulating the manipulation switch 540 of the controller 500, and operates both the fan 310 and the electric heater 320.

Here, the user may set a temperature condition for drying on the display panel 530 by operating the manipulation switch 540 to select cool air drying or warm air drying, and also set an operating time by manipulating the timer 554.

Therefore, cool air or warm air is used to dry the articles received in the second space 620 while moving through the net sheet 230 of the opened main frame 210 and the net sheets 230 of the opened sub-frames 220, and air used to dry the articles is discharged to the outside through the exhaust port 130.

Meanwhile, if there is the concern that the material (fabric) of a drying target may be damaged or deformed when air for drying, such as cool air or warm air, is directly transferred to articles received in the second space 620 partitioned into multiple regions, the medium-scale blocking plate 250 may be coupled to the main frame 210, as shown in FIG. 2, so that the flow of air discharged from the fan 310 is not directly transferred to the material. Also, the blocking plate 240 may be coupled to a sub-frame 220 in a region in which articles not requiring drying are received, among regions of the partitioned second space 620, thus enabling the region to be sealed.

Thereafter, the user selects the cool/warm dry mode controller 552 of the mode selection unit 550 by manipulating the manipulation switch 540 of the controller 500 and operates the fan 310 and the electric heater 320.

Here, the user may set a temperature condition for drying on the display panel 530 by operating the manipulation switch 540 to select cool air drying or warm air drying, and also set an operating time by manipulating the timer 554.

As described above, it can be seen that the present invention adopts in technical spirit the provision of the portable bag assembly having a drying and sterilization function, which is easy to carry and is configured to dry and sterilize articles put in the bag assembly in an inevitable situation in which the washing and drying of the articles are impossible, thus enabling the articles to be maintained in a sanitary state.

In accordance with the present invention having the above configuration, sterilization and drying are performed by a management unit manipulated by a controller on articles individually received in an inner space that is partitioned into multiple regions by a partition unit contained in a bag main body, so that the portable bag assembly is easy to carry and is configured to dry and sterilize articles put in the portable bag assembly in an inevitable situation in which the washing and drying of the articles are impossible, thus enabling the articles to be maintained in a sanitary state.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:

1. A portable bag assembly having a drying and sterilization function, comprising:
   a bag main body configured to form an inner space enabling an article to be received in and removed from the inner space, the partition unit having an openable surface so that access to the inner space is made;
   a partition unit contained in the bag main body and configured to partition the inner space into multiple regions, the partition unit having an openable surface so that access to the inner space is made:
   a bottom frame with mesh so that water from wet articles may be easily drained to the bottom surface of the bag main body;
   a management unit provided in a portion of the bag main body and configured to sterilize an article received in the inner space or to dry a wet article by supplying cool air or warm air to the inner space;
   a controller provided in a portion of the bag main body and electrically connected to the management unit, the controller controlling operation of the management unit; and
   a wireless communication module electrically connected to the controller and configured to receive a control signal required for remote control of the management unit from a predesignated wireless terminal and transfer the control signal to the controller.

2. The portable bag assembly of claim 1, further comprising a two-dimensional (2D) barcode printed on a side surface of the bag main body and configured to record predetermined identification code in the 2D barcode,
   wherein the 2D barcode is scanned via a camera of the wireless terminal and configured to provide a remote control interface for generating the control signal to the wireless terminal.

3. The portable bag assembly of claim 2, wherein:
the identification code recorded in the 2D barcode is an address of a website composed of characters, and
the remote control interface is a mobile application downloaded from the website.

4. The portable bag assembly of claim 2, wherein:
the identification code recorded in the 2D barcode is a remote control information format functionally corresponding to an input button of the controller, and
the remote control information format is extended and registered in a remote control program previously installed in the wireless terminal and configured to provide the remote control interface.

5. The portable bag assembly of claim 1, further comprising a humidity sensor provided in a portion of the bag main body and configured to measure humidity of the inner space,
   wherein the controller determines whether the article received in the inner space has been dried by comparing humidity data measured by the humidity sensor with a preset reference value, and if it is determined that drying of the article has been completed, transmits a drying completion signal to the wireless terminal.

6. The portable bag assembly of claim 1, wherein the management unit includes a fan mounted in the big main body to circulate air through the inner space, an electric heater mounted in the inner space to heat or cool air therein, and a sterilizer mounted in the inner space to radiate light to sterilize the article.

* * * * *